US008568825B2

(12) United States Patent  (10) Patent No.: US 8,568,825 B2
Raj et al.  (45) Date of Patent: Oct. 29, 2013

(54) ULTRA-SENSITIVE SIMULTANEOUS ELECTROCHEMICAL DETERMINATION OF ARSENIC, MERCURY AND COPPER

(75) Inventors: C. Retna Raj, West Bengal (IN); Bikash Kumar Jena, West Bengal (IN)

(73) Assignee: Indian Institute of Technology, West Bengal (IN)

( * ) Notice: Subject to any disclaimer, the term of this patent is extended or adjusted under 35 U.S.C. 154(b) by 505 days.

(21) Appl. No.: 12/427,327

(22) Filed: Apr. 21, 2009

(65) Prior Publication Data
 US 2009/0260984 A1 Oct. 22, 2009

(30) Foreign Application Priority Data

Apr. 22, 2008 (IN) .............................. 755/KOL/2008

(51) Int. Cl.
 *B05D 5/12* (2006.01)
(52) U.S. Cl.
 USPC .................... 427/126.1; 204/400; 427/180
(58) Field of Classification Search
 USPC ...................................................... 427/126.5
 See application file for complete search history.

(56) References Cited

U.S. PATENT DOCUMENTS

| 5,385,708 | A | 1/1995 | Mandler et al. |
| 5,391,270 | A | 2/1995 | Gui et al. |
| 2003/0096115 | A1* | 5/2003 | Kozaki et al. ................. 428/404 |
| 2008/0245670 | A1 | 10/2008 | Compton et al. |

FOREIGN PATENT DOCUMENTS

WO  2007045916 A2  4/2007

OTHER PUBLICATIONS

Bikash et al. (Enzyme-free Amperometric Sensing of Glucose by Using Gold Nanoparticles, 2006).*
Bikash et al. (Highly sensitive and selective electrochemical detection of sub-ppb level chromium(VI) using nano-sized gold particle, 2008).*
Xu et al., "Microwave-irradiated synthesized platinum nanoparticles/carbon nanotubes for oxidative determination of trace arsenic (III)," Electrochemistry Communications 10, 2008, 551-554.
Tongesayi et al., "Electrochemical Detection of Arsenic (III) in the Presence of Dissolved Organic Matter (DOM) by Adsorptive Square-Wave Cathodic Stripping Voltammetry (Ad-SWCSV)," Electroanalysis 20, 2008, No. 4, 434-437.
Yamada et al., "Anodic stripping voltammetry of inorganic species of As3+ and As5+ at gold-modified boron doped diamond electrodes," Journal of Electroanalytical Chemistry 615, 2008, 145-153.
Salimi et al., "Electrochemical detection of trace amount of arsenic (III) at glassy carbon electrode modified with cobalt oxide nanoparticles," Sensors and Actuators B 129, 2008, 246-254.
Cabello-Carramolino et al., "Application of new sol-gel electrochemical sensors to the determination of trace mercury," Analytica Chimica Acta 614, 2008, 103-111.

(Continued)

*Primary Examiner* — Michael Cleveland
*Assistant Examiner* — Austin Murata
(74) *Attorney, Agent, or Firm* — The Webb Law Firm

(57) ABSTRACT

A sensor for the simultaneous detection of inorganic contaminants, As (III), Hg (II) and Cu (II) in water and having a limit of detection of 0.02 ppb, comprising a conducting support having a layer comprised of a three dimensional silicate network comprised of thiol tail groups immobilized with citrate stabilized gold nanoparticles, wherein the gold nanoparticles have a size in the range of 70 to 100 nm.

11 Claims, 4 Drawing Sheets

(56) References Cited

OTHER PUBLICATIONS

Simm et al., "Sonically Assisted Electroanalytical Detection of Ultratrace Arsenic," Anal. Chem., 76, 2004, 5051-5055.

Dai et al., "Anodic Stripping Voltammetry of Arsenic(III) Using Gold Nanoparticle-Modified Electrodes," Anal. Chem., 76, 2004, 5924-5929.

Salaun et al., "Voltammetric Detection of Mercury and Copper in Seawater Using a Gold Microwire Electrode," Anal. Chem., 78, 2006, 5052-5060.

Ivandini, "Electrochemical Detection of Arsenic(III) Using Iridium-Implanted Boron-Doped Diamond Electrodes," Anal. Chem. 78, 2006, 6291-6298.

Hrapovic et al., "Reusable Platinum Nanoparticle Modified Boron Doped Diamond Microelectrodes for Oxidative Determination of Arsenite," Anal. Chem. 79, 2007, 500-507.

Song et al., "Development of a Method for Total Inorganic Arsenic Analysis Using Anodic Stripping Voltammetry and a Au-Coated, Diamond Thin-Film Electrode," Anal. Chem., Mar. 15, 2007, vol. 79, No. 6, pp. 2412-2420.

\* cited by examiner

ULTRA-SENSITIVE SIMULTANEOUS ELECTROCHEMICAL DETERMINATION OF ARSENIC, MERCURY AND COPPER

FIELD OF THE INVENTION

This invention relates to a method for the simultaneous electrochemical determination of inorganic contaminants of water.

This invention further relates to an ultra sensitive, simultaneous electrochemical determination of inorganic contaminants of water such as arsenic, mercury and copper.

BACKGROUND OF THE INVENTION

Arsenic (As) and mercury (Hg) are highly toxic and contamination of water by these toxic elements is a major problem in many countries. Drinking water contaminated with As(III) and Hg(II) is associated with number of diseases such as skin lesions, keratosis, lung cancer, bladder cancer, kidney and respiratory failure, damage in the gastrointestinal tract and nervous system, impairment of speech, hearing and working etc. Contamination of As(III) has been reported in various parts of the world. Mercury is one of the heavy metals, highly toxic and harmful to the environment and human health. World Health Organization (WHO) has set the guidelines value 10 ppb for As(III). On the other hand, the US environmental protection agency (EPA) has set the maximum contaminant level of mercury in drinking water at 2 ppb. Thus determination of trace level of As(III) and Hg(II) at the guideline value set by WHO is of particular importance.

Various methods including hydride generation atomic fluorescence spectrometry, inductively coupled plasma atomic emission spectrometry (ICPAES), inductively coupled plasma mass spectrometry (ICPMS), fluorescence spectrophotometry, atomic absorption spectrometry etc. have been used for the detection of As(III) and Hg(II). Although these methods are successful in detecting As(III) and Hg(II) at sub-picogram to sub-nanogram level, they require expensive instruments, laboratory set-up and high operating cost. In contrast, the electrochemical methods are highly sensitive and involve low cost equipments and laboratory set up. The stripping voltammetric methods provide an efficient and reliable way to detect arsenic and mercury at low concentration. Au coated diamond and glassy carbon (GC) electrode and Au micro wire electrode have been employed for the detection of As(III) and Hg(II). Nevertheless, the major problems associated with the available electrochemical methods are (i) the interference due to other metal ions like Cu(II) present in the natural water (ii) high detection potential and (iii) interference due to supporting electrolyte anions. The concentration of Cu(II) in natural/drinking water is relatively high and it greatly interferes the measurement of As(III) due to the formation of intermetallic compound such as $Cu_3As_2$. Because of the interference due to Cu(II) and other supporting electrolyte anions, simultaneous determination has not been achieved. Furthermore, although As(III) and Hg(II) has been detected individually by electrochemical methods, simultaneous detection without interference from other coexisting ions has not been achieved.

For the electrochemical detection of As(III) and Hg(II), various solid electrodes have been employed in the art. Recently, the nano-sized metal particle electrochemically deposited electrodes have been used for the electroanalysis of As(II). Dai et. al and Simm et. al (Anal. Chem. 2004, 76, 5924-5929, Anal Chem. 2004, 76, 5051-5055) have reported the detection of arsenite using various electrodes. Ivadine et. al (Anal. Chem. 2006, 78, 6291-6298) utilized iridium-implanted boron-doped diamond (BDD) electrode for the detection of As(III) in ppb level. Very recently, Song and Swain (Anal Chem. 2007, 79, 2412-2420) have used the Au-coated diamond thin film electrode for the voltammetric determination of As(III) and As(V). Hrapovic et. al (Anal Chem. 2007, 79, 500-507) very recently reported the reusable Pt nanoparticle modified BDD microelectrodes for the oxidative determination of As(III).

The Au nanoparticle modified electrodes are known to be highly sensitive in the electrochemical detection of As(III). The major problems associated with the available electrochemical methods are (i) the interference due to other metal ions like Cu(II) present in the natural water (ii) high detection potential and (iii) interference due to supporting electrolyte anions. Cu(II) forms intermetallic compound such as $Cu_3As_2$ with As(III) and the accurate measurement of As(III) has not been achieved due to this interference.

In the case of Hg (II), unmodified and chemically modified electrodes have been used for its detection. Microelectrode and microelectrode arrays iridium and Au have been used for the detection of Hg(II) (Anal. Chem 2006, 78, 6291). Au microwire electrode has been recently used for the detection of Hg(II) in seawater (Anal. Chem. 2006, 78, 5052-5060). The major concern with these electrodes is the lack of long term stability and it requires medium exchange or surface regeneration.

PCT/GB06/03957 discloses electrochemical methods and materials for the detection of arsenic. In one aspect, arsenic is detected using a working electrode comprising particulate platinum. In another aspect, arsenic is detected using an electrode comprising indium tin oxide and particulate gold. Also provided are methods for the production of electrodes which involve the electrodeposition of Au onto indium tin oxide. The inventors have used the glassy carbon and indium tin oxide (ITO) electrodes modified with Pt and Au nanoparticles for the detection of As(III). As(III) has been detected on the Pt nanoparticle modified electrode by its oxidation to As(VI) whereas the measurement has been made on the Au nanoparticle by the oxidation of electrodeposited As(0). The detection limit achieved is 2.1 and 5 ppb on Pt and Au nanoparticle modified electrodes, respectively. The interference due to Cu(II) on the Au nanoparticle modified electrode has not been evaluated.

U.S. Pat. No. 5,385,708 entitled "Determination of ultra low levels of mercury" teaches a highly specific and sensitive electrode for the determination of ultra-low levels of mercury and an analytical system based on such electrode. The electrode is a glassy carbon electrode spin-coated with a monolayer of a highly sensitive reagent for the detection of mercury. The analytical method based on the use of this type of electrode is a voltammetric method. Concentrations of the order of as low as about $2.10^{-12}$ Moles mercury can be detected and measured. The reagent is 4,7,13,16,21,24-hexaoxa-1,10-diazabicyclo-[8.8.8]hexacosane for the detection of Hg (II). This measurement is based on the complexation of Hg(II) with the aforementioned complexing agent. The concentration of Hg(II) has been monitored from the stripping current. Because this method is based on the complexation, regeneration of the electrode surface is critically necessary for repeated use.

U.S. Pat. No. 5,391,270 entitled 'Detection and measurement of heavy metals' discloses an improved method for measuring the presence and amount of a variety of metals contained in a sample. In the first step, all of the various forms of each metal are converted to a soluble metallic complex which is capable of being electrochemically reduced. Voltammetry is then used to determine the stripping current or charge characteristic of each metallic complex. Finally, the concentration of each metal can be calculated by insertion of the stripping current or charge value into an equation which correlates peak current or charge values with metal concentration. The metals which can be detected and quantified by using this method are gold, silver, bismuth, cadmium, thallium, and mercury. The concentration of heavy metals is determined using the stripping method. This method is based on the complexation of the metal ions with iodide ion. The metal ions have been converted into complexes of soluble form, which are electrochemically analyzed. The interference due to other metal ions has not been addressed.

In view of the limitations of the prior art and the lack of a sensor that can simultaneously detect and determined inorganic contaminants such as Arsenic (III), Mercury (II) and Copper (II), the need exists in the industry for such a system.

OBJECTS OF THE INVENTION

It is an object of this invention to propose a sensor and a method, for the simultaneous electrochemical determination of inorganic contaminants of water.

It is a further object of this invention to propose a sensor and a method, for the simultaneous electrochemical determination of inorganic contaminants in which simultaneous determination is possible without compromising the sensitivity.

Another object of this invention is to propose a sensor and a method, for the simultaneous electrochemical determination of inorganic contaminants in which there is no interference from the major interferent or surface active reagents in the electrochemical determination.

Yet another object of this invention is to propose a sensor and a method, for the simultaneous electrochemical determination of inorganic contaminants of water, which shows wide linear response.

These and other objects and advantages of the invention will be apparent from the ensuing description and illustrated with the help of the accompanying drawings.

BRIEF DESCRIPTION OF THE ACCOMPANYING DRAWINGS

BRIEF DESCRIPTION OF THE INVENTION

Figure 1:
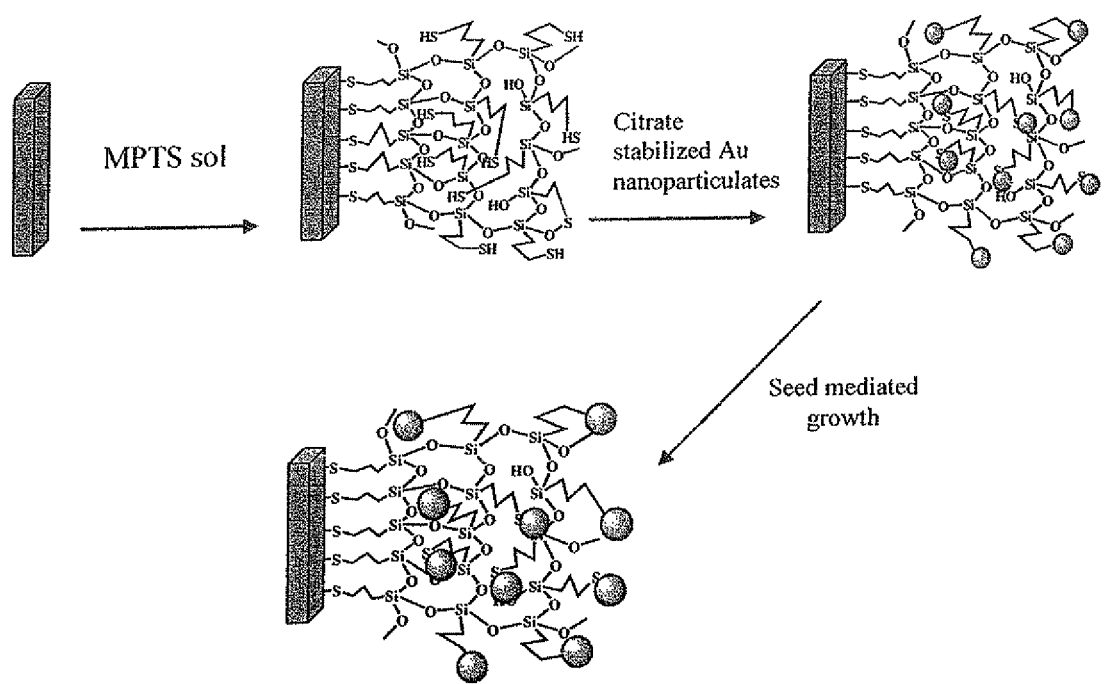
FIG. 1 shows a diagrammatic representation of the scheme for the fabrication of the sensor.

Thus according to this invention is provided a sensor for the simultaneous electrochemical determination of inorganic contaminants of water.

According to this invention is further provided a method for the simultaneous electrochemical determination of inorganic contaminants of water.

In accordance with this invention is developed an ultra sensitive platform based on particulates of Au, for the simultaneous electrochemical detection/determination of inorganic contaminants As(III), Hg(II) and Cu(II) without compromising the sensitivity.

The fabrication of this sensor involves the following procedures: The conducting support is first modified with a layer of sol-gel 3-D silicate network. This network has plenty of —SH functional groups. In this step the conducting support i.e. the electrode is first modified with a thin layer of silicate network derived from (3-mercaptopropyl)trimethoxysilane (MPTS). MPTS is known to form 3-D network structure that is full of thiol tail groups by the hydrolysis and condensation process. The MPTS sol is prepared by dissolving MPTS, methanol and water (as 0.1 M HCl) in the molar ratio of MPTS:methanol:water as 1:3:3 to 2:10:10 and stirring the mixture vigorously for about 10 to 30 minutes. The conducting support is an electrode having a surface selected from polycrystalline gold, coinage metal, platinum and palladium metal.

Au nanoparticulate ensembles have been grown on the thiol groups of the silicate network by colloidal chemical approach. The citrate stabilized nanoparticulates are first self-assembled on the thiol groups of the MPTS network modified electrode by chemisorption. The thiol group has strong affinity to coinage, Pt and Pd metal surfaces and chemisorb on the surface of the metal though the cleavage of S—H bond. The citrate stabilized Au nanoparticulates are obtained by mixing trisodium citrate in a 1-2% (weight/volume), $HAuCl_4$ 1-2% (weight/volume) and $NaBH_4$ in a 0.08-0.1% (weight/volume) and stirring at room temperature in a mole percent of normal pressure. The silicate network modified electrode is soaked in the as-synthesized Au nanoparticulate for 12-18 hr at room temperature under normal pressure.

The size of these nanoparticulates on the silicate network is enlarged by seed mediated growth approach using hydroxylamine and $HAuCl_4$. Hydroxylamine is capable of reducing $Au^{3+}$ to bulk metal and it has been shown that this reaction is accelerated by Au surfaces. The surface-catalyzed reduction of $Au^{3+}$ by hydroxylamine leads to the enlargement of the small particles on the network. Hydroxylamine is added in 0.01 to 5 mM and $HauCl_4$ in 0.01-1 mM. The mixture of hydroxylamine and $HAuCl_4$ is shaken constantly at 200 to 500 rpm, keeping the electrode inside the mixture. The size and morphology of the nanoparticulates on the silicate network have been examined by FESEM and diffuse reflectance spectral (DRS) measurements. The nanoparticulates are randomly distributed throughout the silicate network on the electrode surface and have the size distribution between 70-100 nm and an average size of 85 nm. The FESEM image of this electrode confirms the existence of ensembles of Au-nanoparticles.

A diagrammatic representation of the process is shown in FIG. 1. The sensor has been experimentally tested with commercial and real samples.

The invention will now be explained in greater detail with the help of the following non-limiting example.

EXAMPLE (3-mercaptopropyl)trimethoxysilane (MPTS) sol was prepared by dissolving MPTS, methanol and water (as 0.1 M HCl) in a molar ratio of 1:3:3 and stirring the mixture for 30 minutes. This MPTS sol is added to a polycrystalline gold electrode, which forms a thin layer of a 3-D network on the electrode.

Sodium citrate in 1% (weight/volume), chloroauric acid ($HAuCl_4$) in 1% (weight/volume) and sodium borohydride in 0.08% (weight/volume) were mixed and the mixture stirred together at room temperature and normal pressure. The silicate modified electrode is allowed to stand in this mixture for 12 hrs at room temperature under normal pressure for complete immobilization of the Au nanoparticulate ensembles on the thiol groups of the MPTS network of the modified electrode. Hydroxylamine hydrochloride (0.3 mM) and $HAuCl_4$ (0.3 mM) were mixed and shaken constantly at 200 rpm, keeping the modified electrode inside the mixture to lead to enlargement of the Au-particulates on the network to an average size of 85 nm. This is confirmed by the FESEM image of the sensor.

The sensor thus fabricated is subjected to various experiments, to ascertain the properties thereof.

Square wave anodic stripping voltammetry has been used for the detection of the aforementioned inorganic contaminants. The electrochemical measurements were performed with computer controlled CHI643 electrochemical analyzer. Electrochemical cell consists of three electrodes. Working: nanoparticulate modified electrode; auxiliary: Pt wire; reference: Ag/AgCl saturated with NaCl. Arsenic and mercury were deposited at the potential of −0.35 V for 100 s by the reduction of As(III) and Hg(II) in 1 M HCl. The anodic stripping (reoxidation of As(0) to As(III) and Hg(0) to Hg(II)) of electrodeposited As(0) and Hg(0) was performed in the potential range of −0.35 to 0.7 V at the following optimized parameters; frequency: 40 Hz, amplitude: 20 mV and potential increment: 4 mV. The simultaneous detection of As(III), Cu(II) and Hg(II) parameters; frequency: 40 Hz, amplitude: 20 mV and potential increment: 4 mV. The simultaneous detection of As(III), Cu(II) and Hg(II) has been performed at the same experimental condition as in the case of As(III) and Hg(II).

Figure 2A:
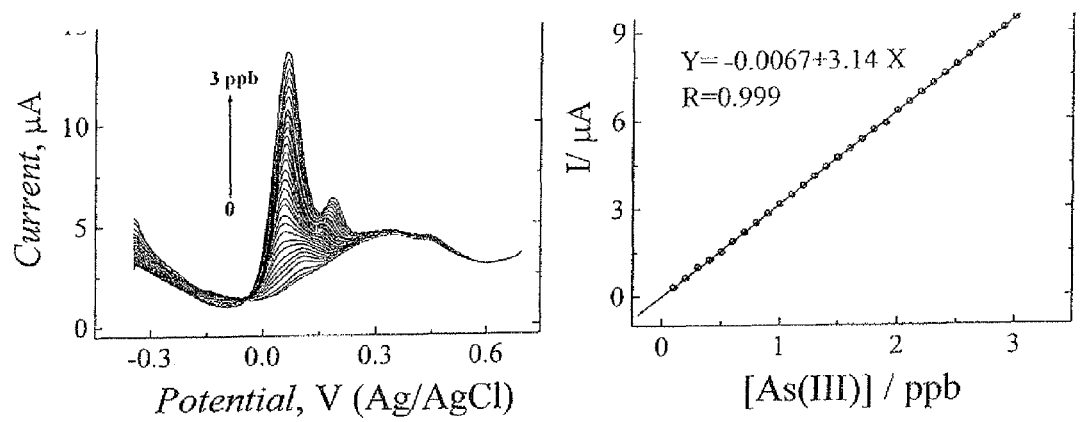
FIG. 2A shows square wave anodic stripping voltammogram for the detection of As(III) in 1 M HCl and the calibration plot.
Figure 2B:
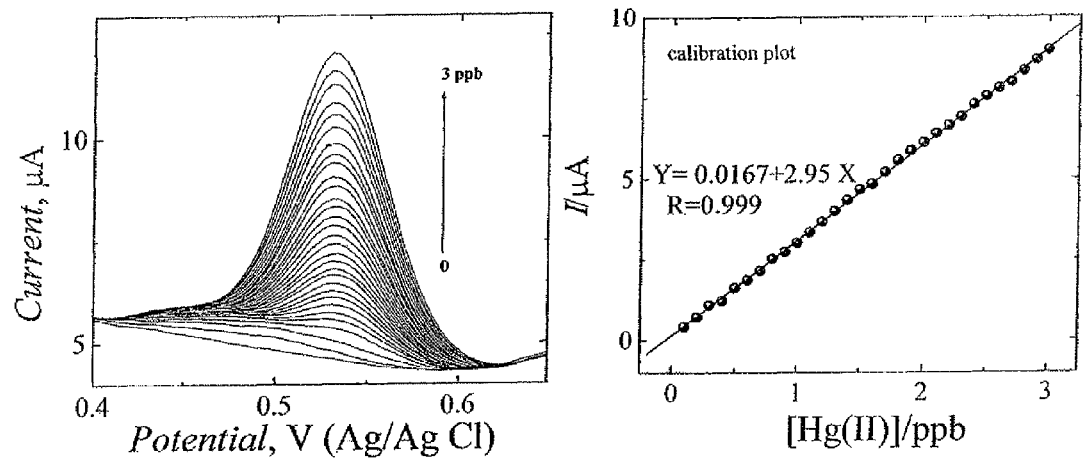
FIG. 2B shows square wave anodic stripping voltammogram for the detection of Hg(II) in 1 M HCl and the calibration plot.
Figure 3:
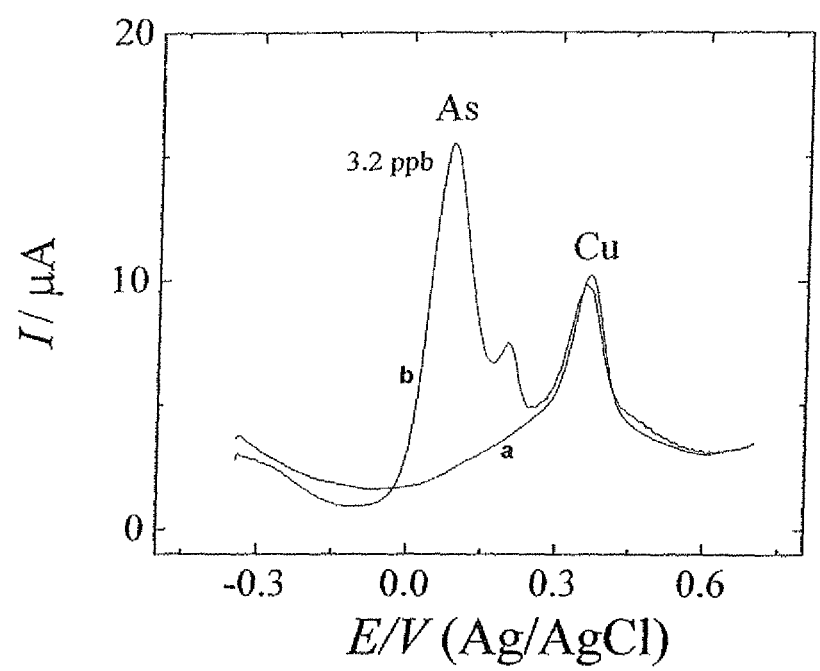
FIG. 3 shows square wave anodic stripping voltammogram for As(III) (3.2 ppb) in the presence (b) of interfering Cu(II) (10 ppb) in 1 M HCl. (a) only Cu(II).
Figure 4:
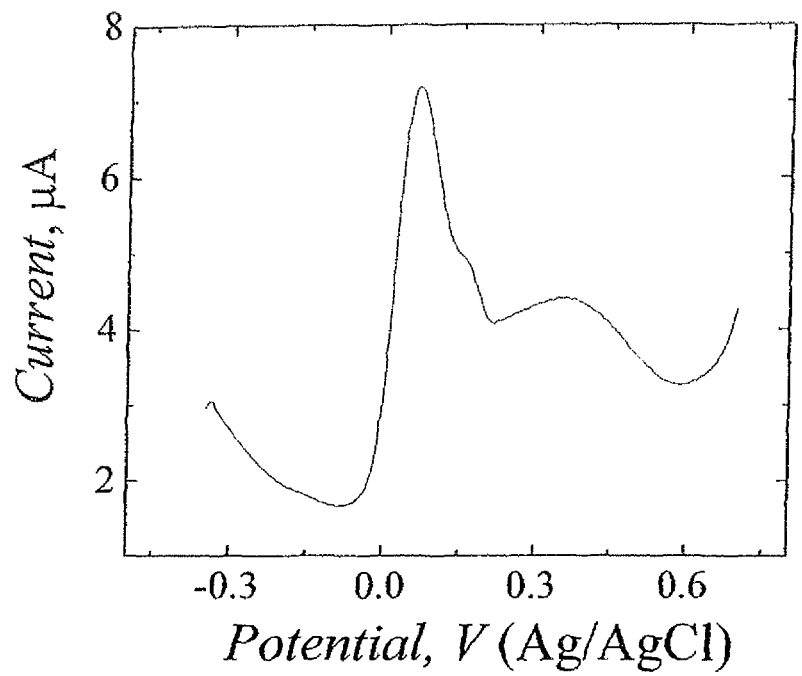
FIG. 4 shows square wave anodic stripping voltammogram for the detection of As(III) in acidified real sample.
Figure 5:
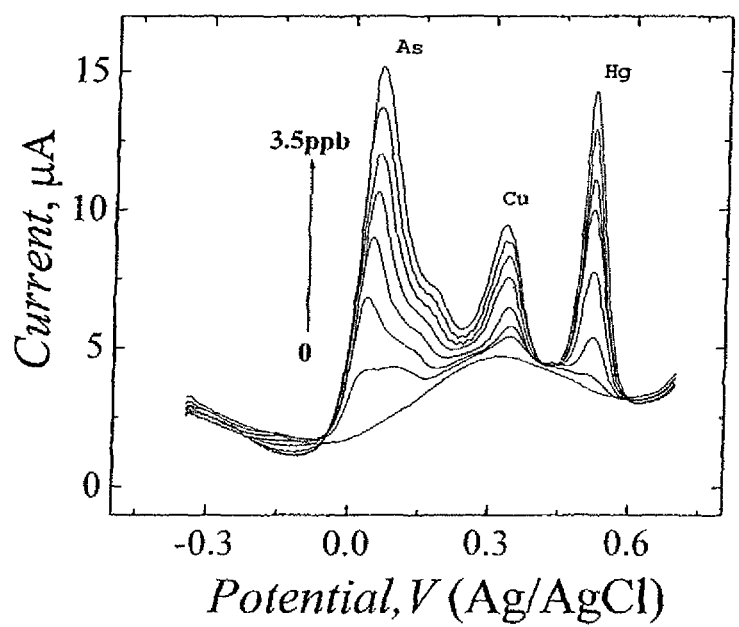
FIG. 5 shows square wave anodic stripping voltammogram for the simultaneous detection of As(III), Hg(II) and Cu(II) in 1 M HCl.

The representative square wave anodic stripping voltammograms for arsenic and mercury are shown in FIGS. 2(A & B). The anodic peak noticed at ~0.05 V in FIG. 2A and ~0.5 V (Ag/AgCl) in FIG. 2B corresponds to the stripping of arsenic and mercury, respectively. It should be mentioned here that the macrosized polycrystalline Au electrode does not show such response. The sensor is highly sensitive and it shows linear response for As(III) and Hg(II). The detection limit (S/N=4) of the sensor towards As(III) and Hg(II) is 0.02 ppb, which is well below the guideline value given by WHO. The sensitivity of the sensor toward As(III) and Hg(II) is 3.14±0.01 and 2.95±0.01 μA/ppb, respectively. Selective detection is a challenging task with the real sample, as the other ions commonly present in the groundwater can be co-deposited and stripped off under the experimental condition used for the detection of As(III) and Hg(II). Particularly Cu(II) is a major interferent in the detection of As(III). The electrodes that have high sensitivity toward As(III) suffer from the interference due to Cu(II). However, the sensor described herein does not suffer from the interference due to Cu(II). Two distinct anodic peaks for As(III) and Cu(II) were observed at 0.06 and 0.035 V, respectively (FIG. 3). The stripping signal obtained for Cu(0) is 300 mV more positive than As (0). The stripping peak position and height for Cu(0) does not change in the presence of As(III), confirming that the sensor does not favor the formation of intermetallic compound (vide supra). Most importantly, presence of Cu(II) does not affect the sensitivity (3.17±0.01 μA/ppb) of the electrode toward As(III); no change in the peak position for stripping of As(0) has been observed. The potential application of the sensor for the detection of As(III) in real sample collected from the arsenic contaminated water (24 North Parganas, West Bengal) has been tested (FIG. 4). The concentration of As(III) in the real sample has been quantified using a standard calibration plot. Because the voltammetric peak for the stripping of As(0), Cu(0) and Hg(0) appears at different potential with a separation of 180-300 mV between the stripping peaks, the simultaneous measurement of all these three ions has been achieved (FIG. 5). The sensitivity of the electrode does not change when As(III), Hg(II) and Cu(II) co-exist. Furthermore, this sensor is free from the interference due to surface active compound exist in real samples. This has been verified by measuring the concentration in the presence of humic acid. Such simultaneous detection has not been reported in the literature. The analytical performance of the sensor is superior to the existing electrodes. Compared with the existing electrodes, this sensor is ultra sensitive, selective, stable for a week and can be used for the simultaneous measurements without compromising the sensitivity. No change in the response has been observed during continuous use for 24 hours.

We claim:

1. A process for manufacturing a sensor for the simultaneous detection of inorganic contaminants of water comprising:
   providing a conducting support;
   adding a (3-mercaptopropyl) trimethoxysilane (MPTS) sol thereto;
   forming a silicate network modified support from the MPTS;
   preparing a mixture containing citrate stabilized gold nanoparticulates;
   soaking the silicate network modified support in the mixture containing citrate stabilized gold nanoparticulates to immobilize the gold nanoparticulates on the silicate network modified support;
   preparing a solution of hydroxylamine and chloroauric acid;
   shaking the solution of hydroxylamine and chloroauric acid; and
   placing the conducting support inside the solution of hydroxylamine and chloroauric acid, to obtain the sensor,
   wherein shaking the solution of hydroxylamine and chloroauric acid occurs at 200 to 500 rpm.

2. The process as claimed in claim 1, wherein the conducting support is an electrode having a surface comprising polycrystalline gold, coinage metal, platinum or palladium.

3. The process as claimed in claim 1, wherein the MPTS sol is prepared by dissolving MPTS, methanol and dilute hydrochloric acid into a mixture and stirring the mixture.

4. The process as claimed in claim 3, wherein the MPTS, methanol and hydrochloric acid are present in a molar ratio of 1:3:3 to 2:10:10.

5. The process as claimed in claim 3, wherein a 0.1 M hydrochloric acid is used.

6. The process as claimed in claim 3, wherein the mixture is stirred for about 10 to 30 minutes.

7. The process as claimed in claim 1, wherein the citrate stabilized gold nanoparticles are prepared by mixing trisodium citrate in 1-2% (weight/volume); $HAuCl_4$ in 1 to 2% (weight/volume); and sodium borohydride in 0.08 to 0.1% (weight/volume), at room temperature and normal pressure.

8. The process as claimed in claim 1, wherein the silicate network modified support is soaked in the mixture containing citrate stabilized gold nanoparticles for 12 to 18 hours at room temperature and normal pressure.

9. The process as claimed in claim 1, wherein 0.01-5 mM of hydroxylamine hydrochloride is used.

10. The process as claimed in claim 1, wherein 0.01 to 1 mM of chloroauric acid ($HAuCl_4$) is used.

11. The process of claim 1, wherein said sensor simultaneously and electrochemically detects As(III), Hg(II), and Cu(II).

* * * * *